United States Patent [19]

Holtkamp, Sr.

[11] Patent Number: Plant 7,110

[45] Date of Patent: Jan. 16, 1990

[54] AFRICAN VIOLET PLANT NAMED SCORPIO

[76] Inventor: Reinhold Holtkamp, Sr., Werther Strasse 112, D4294 Isselburg, Fed. Rep. of Germany

[21] Appl. No.: 310,760

[22] Filed: Feb. 15, 1989

[51] Int. Cl.[4] ..... A01H 5/00

[52] U.S. Cl. ..... Plt./69

[58] Field of Search ..... Plt./69

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A new and distinct cultivar of African violet named Scorpio characterized by its single, lilac flowers with darker center radiating into the 2 small petals; strong, upright flower stems that curve toward the center to form a compact bouquet above the leaves; bright green, slightly serrated girl-type leaves; profuse flowering, vigorous growth habit, flowering 10–11 weeks after potting, and its long lasting and non-dropping flowers.

1 Drawing Sheet

The present invention comprises a new and distinct cultivar of African violet plant, botanically known as *Saintpaulia ionantha,* and hereinafter referred to by the cultivar name Scorpio.

The new cultivar was referred to during the breeding and selection process by the designation I II/29 and is a product of a planned breeding program. The new cultivar was originated from a cross made by me in the controlled breeding program in Haffen, Federal Republic of Germany. The female, or seed parent was a cultivar designated F 38/6. The male, or pollen parent was a cultivar designated G 24/1.

Scorpio was discovered and selected by me as a flowering plane within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Scorpio has not been observed under all possible environmental conditions. The phenotype may vary significantly with variations in environment such as temperature, light intensity and day length. The following observations, measurements and values describe the new cultivar as grown in Haffen, West Germany and Nashville, Tenn. under greenhouse conditions which closely approximate those generally used in commercial practice.

The following traits have been repeatedly observed and are determined to be basic characteristics of Scorpio, which in combination distinguish this African violet as a new and distinct cultivar:

(1) Strong, upright flower stems curving toward the center.

(2) Single, lilac flowers with darker center.

(3) Profuse flowering.

(4) Each plant carries 8–9 and more upright flower stems each of which carries 6–8 and more flowers.

(5) Long lasting, non-dropping flowers.

(6) Vigorous grower.

(7) Plant saleable 10 to 11 weeks after potting.

(8) Seed capsules push slightly through.

(9) Bright green, girl-type leaves, wavy, slightly serrated with a bright light green center.

(10) After maturity the flowers dry off, and remain on the peduncle without becoming infected by botrytis.

Scorpio is similar in certain respects to Taurus which has the same parents. The leaves and the shape of the flowers are similar. However the flowers of Scorpio are lighter in color and larger in size.

The accompanying color photographic drawing shows a typical specimen plant of the new cultivar. The colors appearing in the photograph are as true as possible with color illustrations of this type.

In the following description, color references are made to the Royal Horticultural Society Colour Chart (R.H.S.) except where general colors of ordinary significance are referred to. Color values were taken under natural sunlight conditions at approximately 1 p.m. in Nashville, Tenn.

Botanical classification: *Saintpaulia ionantha,* Ramat., c.v. Scorpio.

Parentage:

*Male parent.*—G 24/1.

*Female parent.*—F 38/6.

Propagation: The new cultivar holds its distinguishing characteristics through successive propagations by leaf cuttings.

Plant: From 9 cm to 10 cm tall when grown in pots, and approximately 18–20 cm in diameter when fully grown.

*Leaves.*—General form: Round, girl-type. Diameter: 60–70 mm. Texture: Velvety. Aspect: Wavy, shiny, slightly hairy, slightly serrated, bright light green center. Veins: Upperside: well visible, greenish white radiating from the center; underside: very well pronounced, light green, shiny, on young leaves slightly purplish. Color (upperside): Yellow-Green Group 146 A Color (underside): Greyed-Green Group 194 D with touches of Greyed-Purple 183 D. Petiole: Strong upright, light green with purplish touch on side towards flowers, hairy.

*Flowers.*—Buds: Bell-shaped, 8–9 mm just before opening, lilac. Sepals: Five (5). Color: Purplish green. Calyx: Shape: Funnel-shaped. Aspect: Spear-shaped, hairy. Peduncle: Character: Strong upright, hairy. Color: Purplish brown. Individual flowers: Size: 40–45 mm. Shape: Single violet-shaped (3 large and 2 small petals). Color (upperside): Purple-Violet Group 82 ranging from B in the center to D. Under cooler temperatures and more intensive lighting, the lilac color tends to intensify. Color (underside): Purple-Violet Group 82 C to D. Borne: Each flower stem carries 6–8 and more flowers on strong, upright peduncle that are free standing above the leaves, thereby forming a compact bouquet. Flowering Habit: Flowers 10–11 weeks after potting.

*Reproductive organs.*—Stamens: Two (2). Anthers: 2 composed of 4 anther cells, seed capsule pushes slightly through. Filaments: Yellowish green, 5 mm long. Pollen Color: Yellow Group 7 A. Styles: 7 mm long, purple, base of ovary light green and hairy.

*Roots.*—Normally developed, white when young, turning slightly brownish when older.

Disease resistance: Good.

General observations: Scorpio has a very attractive appearance due to its bright green slightly serrated leaves with a light green center. A tight bouquet of flowers free standing above the leaves develops after approximately 10–11 weeks. Each of the 8–9 and more strong flower stems carries 6–8 and more lilac, single violet-shaped flowers. In the center of the flower the lilac color is darker and radiates into the two small petals. Occasionally, 1–2 additional very small petals may develop. The flowers are long-lasting and non-dropping.

I claim:

1. A new and distinct cultivar of African violet named Scorpio, as described and illustrated, and particularly characterized by its single, lilac flowers with darker center radiating into the 2 small petals; strong, upright flower stems that curve toward the center to form a compact bouquet above the leaves; bright green, slightly serrated girl-type leaves; profuse flowering, vigorous growth habit, flowering 10–11 weeks after potting, and its long lasting and non-dropping flowers.

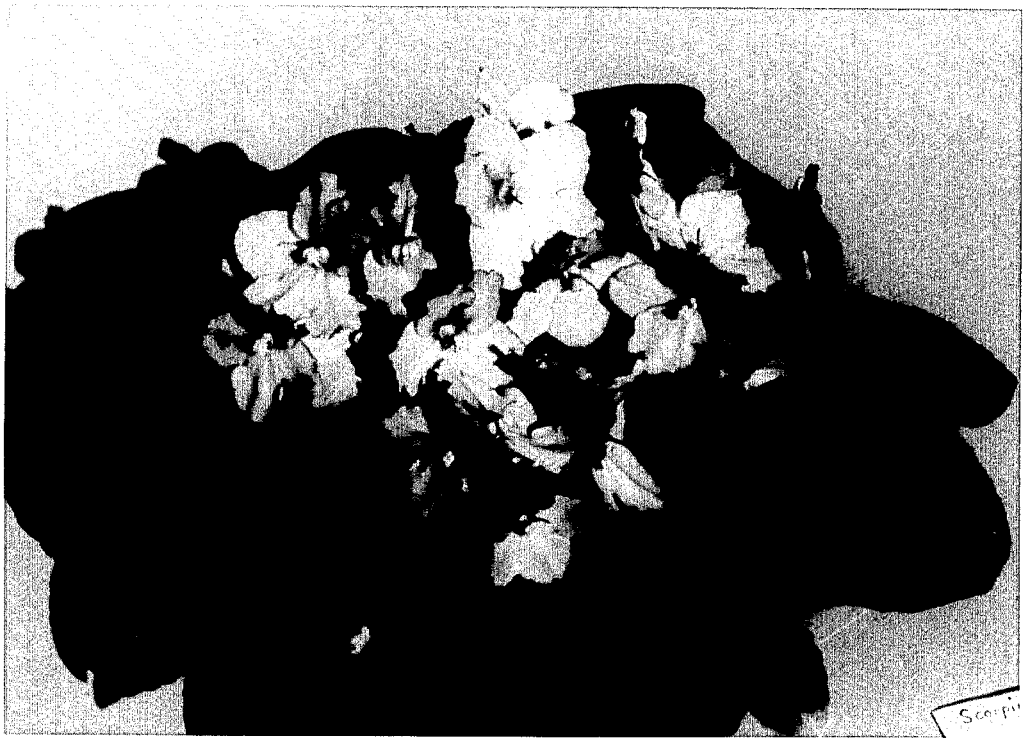

* * * * *